(12) United States Patent
Bunch et al.

(10) Patent No.: US 10,065,029 B2
(45) Date of Patent: Sep. 4, 2018

(54) MECHANICAL DILATOR

(71) Applicant: Cook Medical Technologies LLC, Bloomington, IN (US)

(72) Inventors: Tyler J Bunch, Bloomington, IN (US); Ram H Paul, Jr., Bloomington, IN (US); Gary L Neff, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 618 days.

(21) Appl. No.: 14/636,547

(22) Filed: Mar. 3, 2015

(65) Prior Publication Data

US 2015/0246211 A1  Sep. 3, 2015

Related U.S. Application Data (60) Provisional application No. 61/947,156, filed on Mar. 3, 2014.

(51) Int. Cl.
*A61M 29/02* (2006.01)
*A61M 16/04* (2006.01)
(Continued)

(52) U.S. Cl.
CPC ........ *A61M 29/02* (2013.01); *A61M 16/0472* (2013.01); *A61M 25/0074* (2013.01); *A61M 29/00* (2013.01); *A61M 2025/0024* (2013.01)

(58) Field of Classification Search
CPC .. A61M 29/02; A61M 29/00; A61M 25/0074; A61M 2025/0024; A61M 16/0472; A61B 1/31; A61B 1/32
(Continued)

(56) References Cited

U.S. PATENT DOCUMENTS 2,007,179 A    7/1935 Bullis
4,682,981 A *  7/1987 Suzuki ................. A61M 25/06
                                                   604/104
(Continued)

FOREIGN PATENT DOCUMENTS

DE    10 2011 081 615 A1    2/2013
WO    WO 2009/050478 A1     4/2009

OTHER PUBLICATIONS

International Preliminary Report on Patentability for PCT/US2015/018493, dated Jun. 9, 2016, 10 pp.
(Continued)

*Primary Examiner* — Gregory Anderson
*Assistant Examiner* — Margaret Luarca
(74) *Attorney, Agent, or Firm* — Brinks Gilson & Lione (57) ABSTRACT

A dilator may include a leading portion that includes a leading end coupled to a leading stem. The dilator may further include a trailing portion that includes a trailing end coupled to a trailing shaft. The dilator may also include a segmented body disposed between the leading end and the trailing end. The segmented body may include a plurality of segments disposed circumferentially around the leading stem. The leading stem may extend through a passageway of the segmented body, an opening of the trailing end and a channel of the trailing shaft. The leading stem and the trailing shaft may be configured to move longitudinally relative to one another to radially outwardly expand the segmented body.

20 Claims, 8 Drawing Sheets

(51) Int. Cl.
*A61M 25/00* (2006.01)
*A61M 29/00* (2006.01)

(58) Field of Classification Search
USPC ............... 128/200.26; 606/4, 192, 198, 191; 604/107, 184
See application file for complete search history.

(56) References Cited

U.S. PATENT DOCUMENTS

| | | | |
|---|---|---|---|
| 5,994,383 | A | 11/1999 | Dyer et al. |
| 6,059,752 | A | 5/2000 | Segal |
| 6,231,875 | B1 | 5/2001 | Sun et al. |
| 6,482,799 | B1 | 11/2002 | Tuse et al. |
| 6,899,890 | B2 | 5/2005 | Kirschner et al. |
| 7,179,849 | B2 | 2/2007 | Terry |
| 7,198,800 | B1 | 4/2007 | Ko |
| 7,608,099 | B2 * | 10/2009 | Johnson ............... A61F 2/95 606/108 |
| 7,670,967 | B2 | 3/2010 | Runge et al. |
| 2003/0007939 | A1 | 1/2003 | Murad |
| 2006/0003969 | A1 | 1/2006 | Manandhar |
| 2006/0099550 | A1 | 5/2006 | Faasse et al. |
| 2007/0078116 | A1 | 4/2007 | Lane |
| 2007/0179602 | A1 | 8/2007 | Wright |
| 2008/0077099 | A1 | 3/2008 | House |
| 2008/0153122 | A1 | 6/2008 | Cantor et al. |
| 2009/0076584 | A1 * | 3/2009 | Mao ............... A61F 2/91 623/1.11 |
| 2009/0238867 | A1 | 9/2009 | Jenkins et al. |
| 2010/0106103 | A1 | 4/2010 | Ziebol et al. |
| 2010/0190748 | A1 | 7/2010 | Baker et al. |
| 2010/0215643 | A1 | 8/2010 | Clevenger et al. |
| 2010/0280450 | A1 * | 11/2010 | Jain ............... A61M 25/0074 604/96.01 |
| 2011/0009831 | A1 | 1/2011 | Burkholz et al. |
| 2011/0150961 | A1 | 6/2011 | Perry et al. |
| 2011/0190865 | A1 * | 8/2011 | McHugo ............... A61F 2/95 623/1.11 |
| 2012/0183588 | A1 | 7/2012 | Supamahitorn et al. |
| 2013/0025588 | A1 * | 1/2013 | Bosel ............... A61M 16/0434 128/200.26 |

OTHER PUBLICATIONS

Invitation to Pay Additional Fees with Communication Relating to the Results of the Partial International Search for PCT/US2015/018493, dated Jun. 18, 2015, 5 pp.

International Search Report and Written Opinion for PCT/US2015/018493, dated Aug. 27, 2015, 16 pp.

* cited by examiner

FIG. 8

MECHANICAL DILATOR

This application claims the benefit under 35 U.S.C. § 119(e) of U.S. Provisional Application No. 61/947,156, filed Mar. 3, 2014, which is hereby incorporated by reference herein.

BACKGROUND

1. Technical Field

The present invention relates generally to medical devices and, in particular, to a dilator and, more particularly, to a mechanical dilator.

2. Background Information

Dilators are widely used in medical procedures for dilating or expanding a body opening or channel of a patient. For example, a dilator may be used to open a stoma in the tracheal wall to provide an air passageway. In another example, a dilator may be used to within a vessel to flatten, crack or score plaque against the vessel wall.

Dilators often include a hydraulic balloon that is inflated to cause the dilation or expansion of the dilator. A fluid such as a saline solution may be pumped into the balloon. One problem with the use of a balloon dilator is that the balloon may burst which may cause damage to the patient. Furthermore, the force that the balloon may apply to a body opening or channel is limited by the pressure that may be applied to the balloon. Moreover, balloon dilators may be provided in various sizes so that a desired size may be selected depending on a particular size of the body opening or channel. However, if a particular size is selected and during the procedure the size is found to be incorrect, the currently used balloon dilator may be discarded and another balloon dilator may need to be selected. Therefore, it is desired to provide further improved dilators that may have increased resistance to failure, have increased ability to apply a force to a body opening or channel, and have a size that is adjustable for dilating a wide range of body openings.

SUMMARY

The problems of the prior art are addressed by the dilator of the present invention. In one form thereof, the dilator may include a leading portion that includes a leading end coupled to a leading stem. The dilator may further include a trailing portion that includes a trailing end coupled to a trailing shaft. The trailing end may have an opening, and the trailing shaft may have a channel. The dilator may also include a segmented body disposed between the leading end and the trailing end. The segmented body may have a passageway extending between a proximal end and a distal end, and the segmented body may include a plurality of segments disposed circumferentially around the leading stem. The leading stem may extend through the passageway of the segmented body, the opening of the trailing end and the channel of the trailing shaft. The leading stem and the trailing shaft may be configured to move longitudinally relative to one another to radially outwardly expand the segmented body.

BRIEF DESCRIPTION OF THE DRAWINGS

The invention may be more fully understood by reading the following description in conjunction with the drawings, in which.

DETAILED DESCRIPTION

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the dilator, as well as the axial ends of component features of the dilator. The term "proximal" is used in its conventional sense to refer to the end of the dilator (or component thereof) that is closest to the operator during use of the device. The term "distal" is used in its conventional sense to refer to the end of the dilator (or component thereof) that is initially inserted into the patient, or that is closest to the patient during use.

Figure 1A:
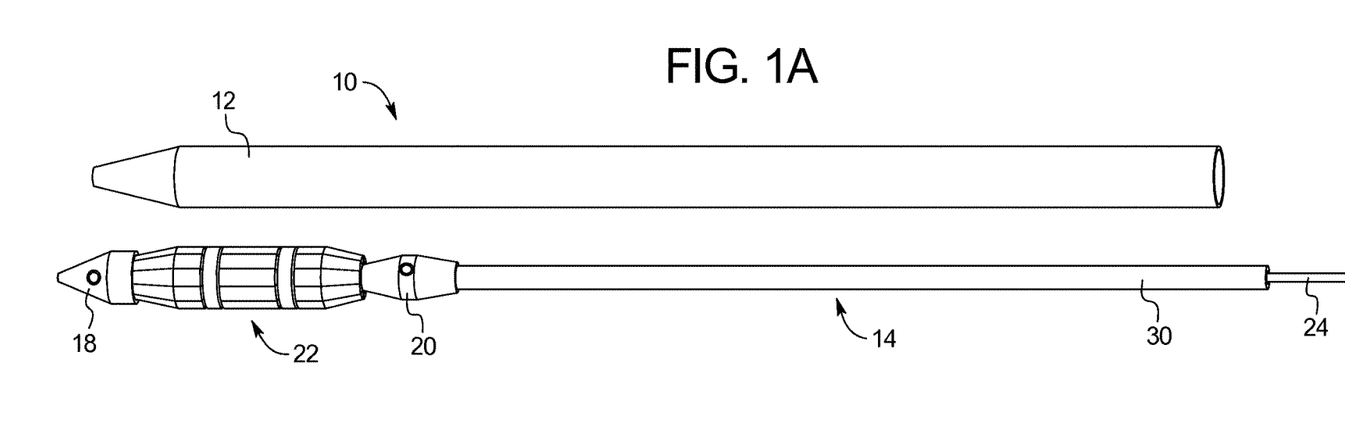
FIG. 1A is a perspective view of the components of a dilator system according to an embodiment of the present application.

In FIG. 1A, a dilator system 10 is shown that includes a sheath 12 and a dilator 14 configured to be at least partially disposed in the sheath 12. The sheath 12 may be configured to expand radially outward when the dilator 14 expands radially outward. As such, the sheath 12 may comprise or be an elastic material. For example, the elastic material may be a polymer such as nylon, polyurethane, polyvinyl chloride, polyester, polyether block amide, polyamide, silicone, polyisoprene, or a blend of one or more of the foregoing. Other non-limiting polymer classes that are also suitable for formation of the elastic material include styrene butadiene styrene (SBS) polymers such as Kraton®, Dynaflex® and Santoprene®, vinyl compounds, silicone rubber materials such as poly-dimethyl siloxane, thermoplastic polyester elastomers (TPEs), polyether block amides such as Pebax®, nitrile, natural rubber, neoprene, ethylene propylene diene monomer (EPDM) rubber, styrene-butadiene rubber (SBR). The sheath 12 may form a protective layer for the dilator 14. For example, the sheath 12 may prevent tissue and/or fluid from entering into the dilator 14. The dilator 14 and the sheath 12 are shown in FIG. 1A as separate to better show the dilator 14. The other example dilators 14 that are described herein are also shown without a sheath 12 to better show the dilator, but any of the dilators 14 described herein may be part of a dilator system 10 that includes a sheath 12.

Figure 1B:
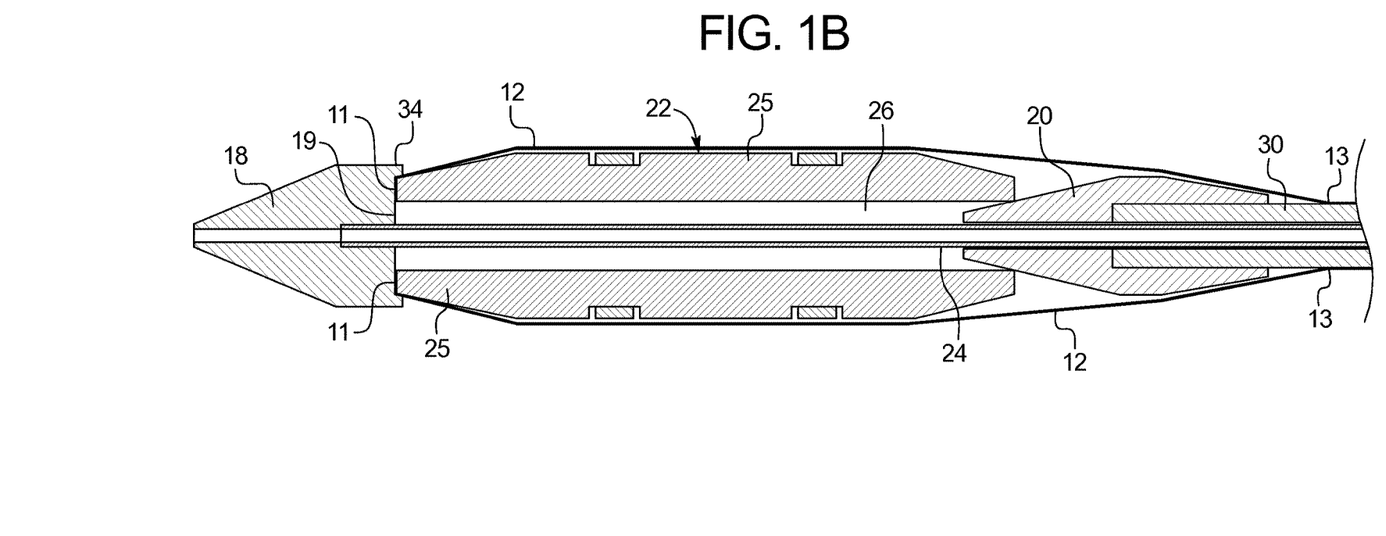
FIG. 1B is a cross-sectional view of the dilator with a permanently affixed sheath.

Although the sheath 12 in FIG. 1A may be a removable sheath 12 that may be slid onto the dilator 14 during use and retained by a squeeze fit, snap fit or by the physician, an alternative design for the sheath 12 is shown in FIG. 1B where the sheath 12 is permanently affixed to the dilator 14. For example, the distal end 11 of the sheath 12 may be bonded to the leading end 18 with an adhesive or other bonding technique. As shown, the distal end 11 of the sheath 12 may be bonded to a proximal facing surface 19 of the leading end 18 between the leading end 18 and the distal end of the segments 25. The sheath 12 preferably surrounds the entire length of the segmented body 22 and extends proximally to the trailing shaft 30. As shown, the proximal end 13 of the sheath 12 may be bonded to the outer diameter of the trailing shaft 30 with an adhesive or other bonding technique.

Figure 1C:
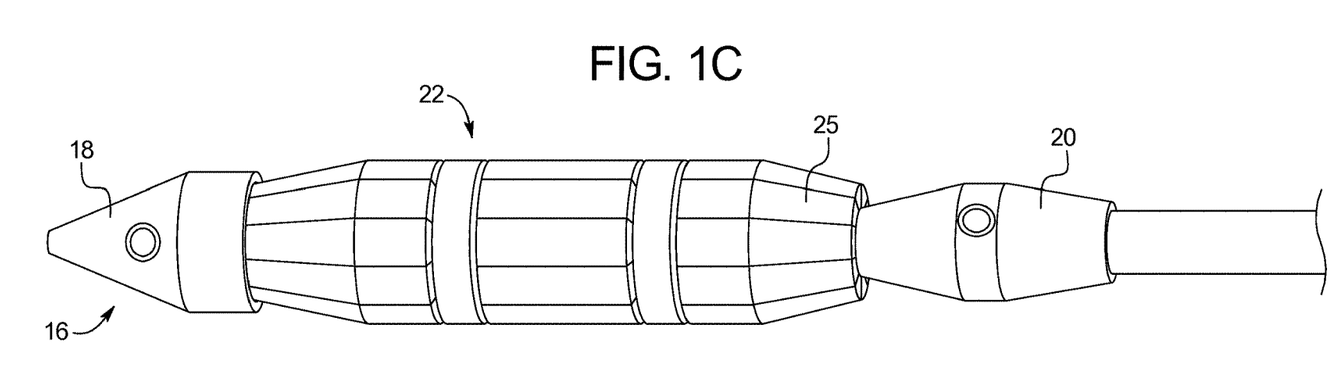
FIG. 1C is a side view of the dilator of the system of FIG. 1A in a collapsed configuration.
Figure 1D:
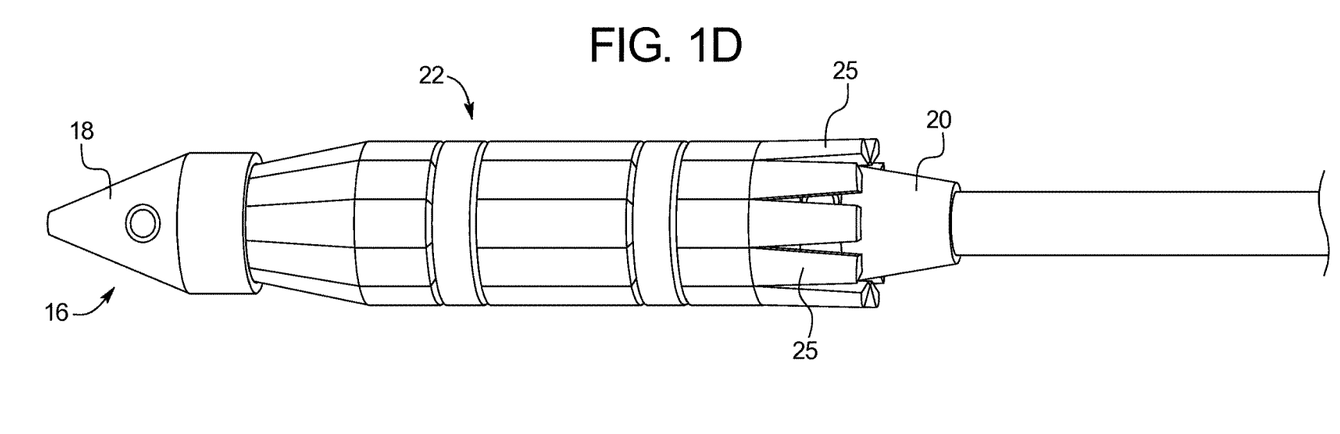
FIG. 1D is a side view of the dilator of the system of FIG. 1A in an expanded configuration.
Figure 1E:
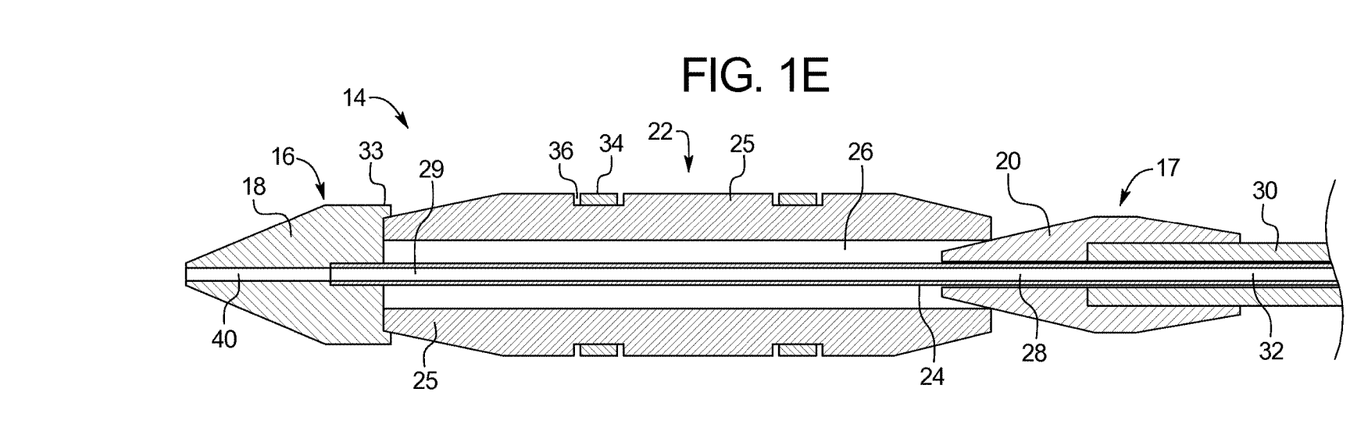
FIG. 1E is a cross-sectional view of the dilator of FIG. 1C.
Figure 1F:
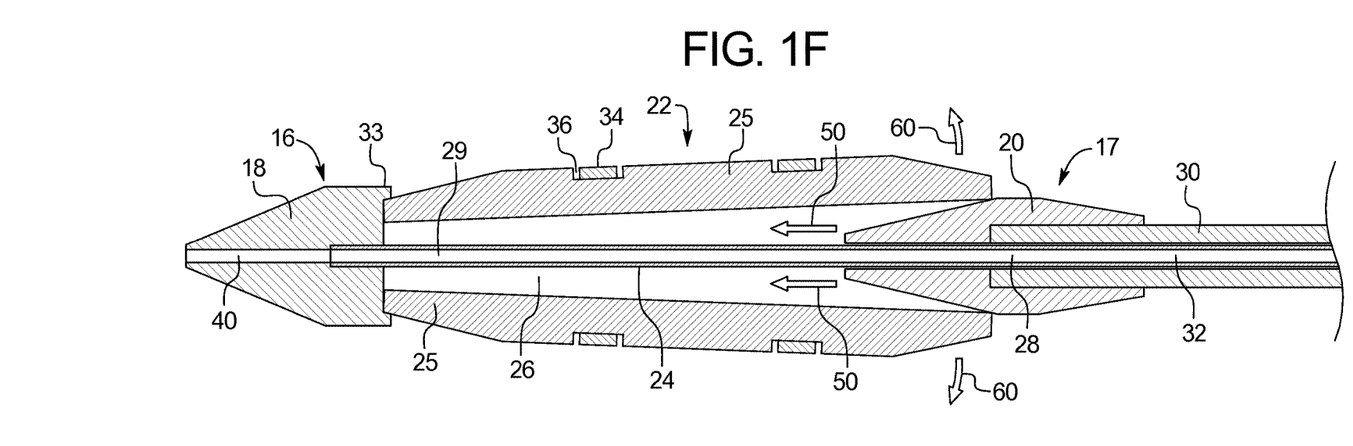
FIG. 1F is a cross-sectional view of the dilator of FIG. 1D.

In FIG. 1C, a distal portion of the dilator 14 is shown in a retracted configuration while, in FIG. 1D, the distal portion of the dilator 14 is shown in an expanded configuration. FIG. 1E and FIG. 1F are cross-sectional views of the dilator 14 showing the internal structure of FIGS. 1C and 1D, respectively. The dilator 14 may include a leading portion 16 that includes a leading end 18 coupled to a leading stem 24, and a trailing portion 17 that includes a trailing end 20 coupled to a trailing shaft 30. The trailing end 20 may include an opening 28, and the trailing shaft 30 may include a channel 32. For example, the trailing shaft 30 may be an elongated tubing. The leading stem 24 may be an elongated tubing, rod, wire, etc. The leading stem 24 may be attached to the leading end 18 and the trailing shaft 30 may be attached to the trailing end by, for example, an adhesive, engaging threads, welded, or a snap-fit. For instance, as illustrated in FIGS. 1E and 1F, the trailing shaft 30 may be disposed within the opening 28 of the trailing end 20, and the leading stem 24 may be disposed within an opening 40 of the leading end 18. Alternatively, the leading portion 16 may be a single piece construction and/or the trailing portion 17 may be a single piece construction.

The channel 32 of the trailing shaft 30 may extend between a distal end and a proximal end of the trailing shaft 30, and the opening 28 of the trailing end 20 may extend between a distal end and a proximal end of the trailing end 20. The channel 32 and the opening 28 may be a continuous opening to provide a passage for the leading stem 24 to extend through. Thus, the leading stem 24 may be at least partially disposed within the channel 32 and the opening 28. The leading stem 24 may move or slide longitudinally within the channel 32 and the opening 28. Therefore, the distance between the leading end 18 and the trailing end 20 may be adjusted longitudinally. For example, the leading end 18 and the trailing end 20 may be both moved, or only one of the leading end 18 or the trailing end 20 may be move while the other end remains stationary.

The proximal ends of the leading stem 24 and the trailing shaft 30 may be operated by a user. For example, the leading stem 24 may extend beyond the trailing shaft 30 at a proximal end, as illustrated in FIG. 1A. A user may independently grasp the leading stem 24 and the trailing shaft 30 in order to move the leading end 18 and the trailing end 20 longitudinally relative to one another. Alternative, the proximal ends of the leading stem 24 and the trailing shaft 30 may be engaged or attached to an actuation handle that controls the relative movement of the leading stem 24 and the trailing shaft 30 similar to that described with regard to a user. For example, the actuation handle may push and pull the leading stem 24 and/or the trailing shaft 30. The actuation handle may further include a locking mechanism to in order to lock the relative positions of the leading stem 24 and the trailing shaft 30.

The dilator 14 may also include a segmented body 22 disposed between the leading end 18 and the trailing end 20. The segmented body 22 may have a passageway extending between a proximal end and a distal end of the segmented body 22, and the leading stem 24 may extend through the passageway 26 of the segmented body 22. Furthermore, the segmented body 22 may include a plurality of segments 25 disposed circumferentially around the leading stem 24. As described above, the leading stem 24 may extend through the opening 28 of the trailing end 20 and the channel 32 of the trailing shaft 30. The leading stem 24 and the trailing shaft 30 may be configured to move longitudinally relative to one another so that at least one of the leading end 18 or the trailing end 20 enters the passageway 26 of the segmented body 22 to radially outwardly expand the segmented body 22. Thus, the segmented body 22 may be configured to expand radially outward away from the leading stem 24 when at least one of the leading end 18 or the trailing end 20 enters the passageway 26. For example, in FIG. 1F, arrows 50 show longitudinal movement of the trailing end 20 into the passageway 26 of the segmented body 22. Arrows 60 show the outward radial movement of the segmented body 22 as a result of the trailing end 20 entering into the passageway 26. Thus, the longitudinal movement of the leading portion 16 and the trailing portion 17 relative to one another may control the expansion and collapse of the segmented body 22. As the distance between the leading end 18 and the trailing end 20 decreases, a circumference of the segmented body 22 may progressively increase. Only one of the leading end 18 or the trailing end 20 or both of the leading end 18 and the trailing end 20 may enter the passageway 26. FIGS. 1A-1F show one example of a dilator 10 where the trailing end 20 and not the leading end 18 is configured to enter the passageway 26.

Figure 2A:
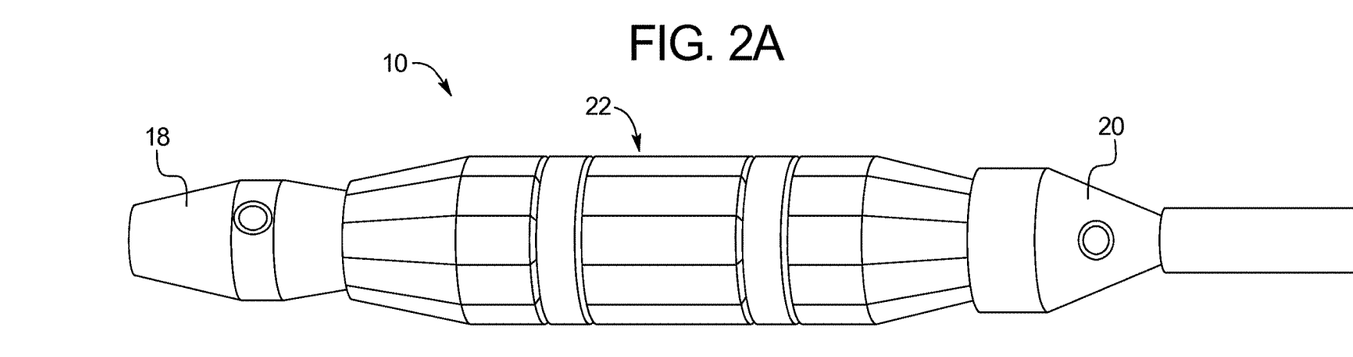
FIG. 2A is a side view of a dilator with an expanding distal end in a collapsed configuration according to an embodiment of the present application.
Figure 2B:
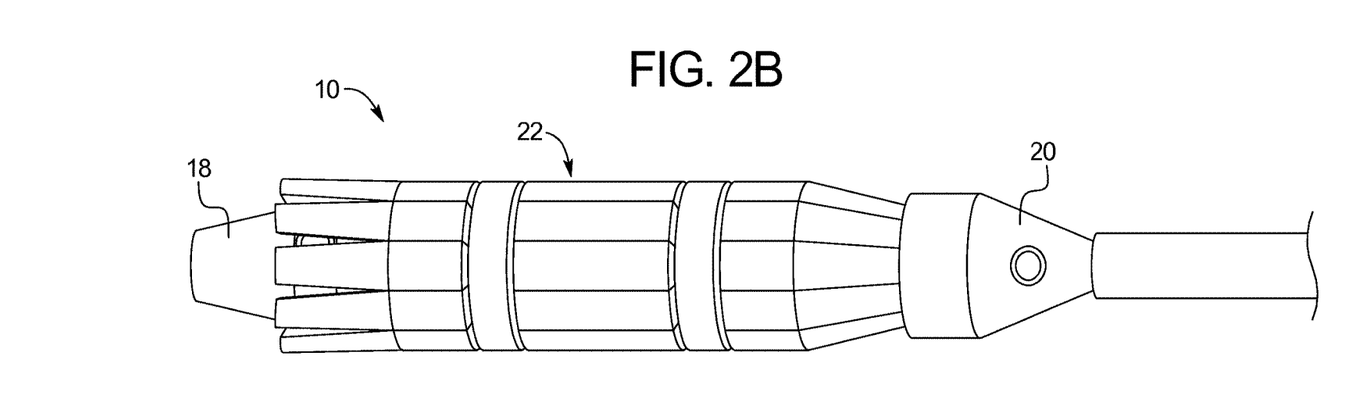
FIG. 2B is a side view of the dilator of FIG. 2A in an expanded configuration.

FIGS. 2A and 2B show another example of a dilator 10 in collapsed and expanded configurations, respectively, in which a leading end 18 and not the trailing end 20 is configured to enter the passageway. The dilator 10 of FIGS. 2A and 2B is similar to that shown in FIGS. 1A-1F except that the leading end 18 is configured to enter the segmented body 22 while the trailing end 20 is configured to not enter the segmented body 22.

Figure 3A:
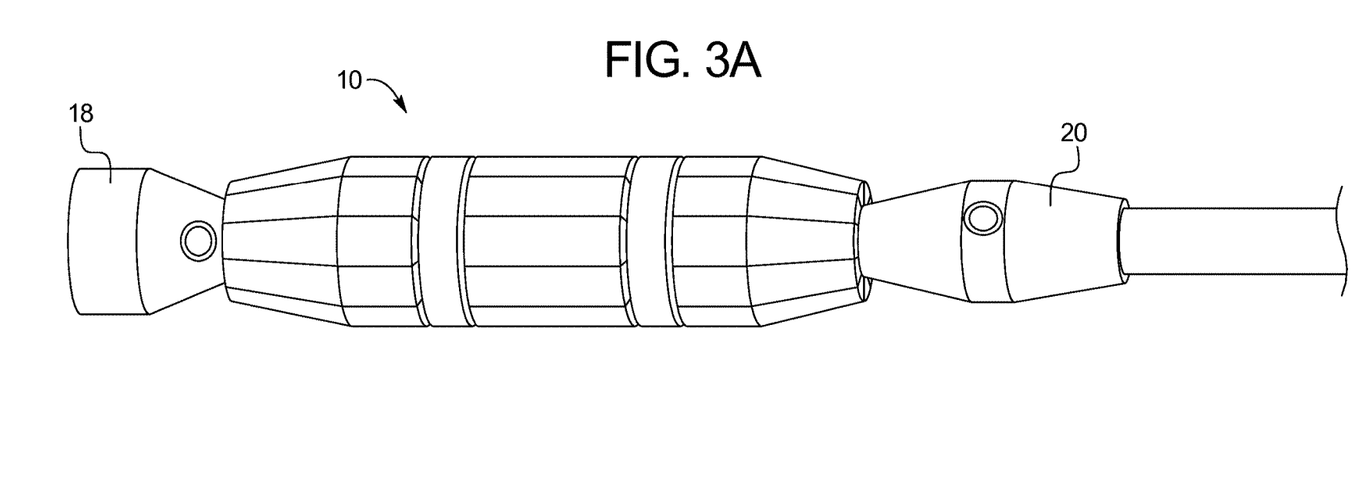
FIG. 3A is a side view of a dilator with an expanding proximal end and distal end in a collapsed configuration according to an embodiment of the present application.
Figure 3B:
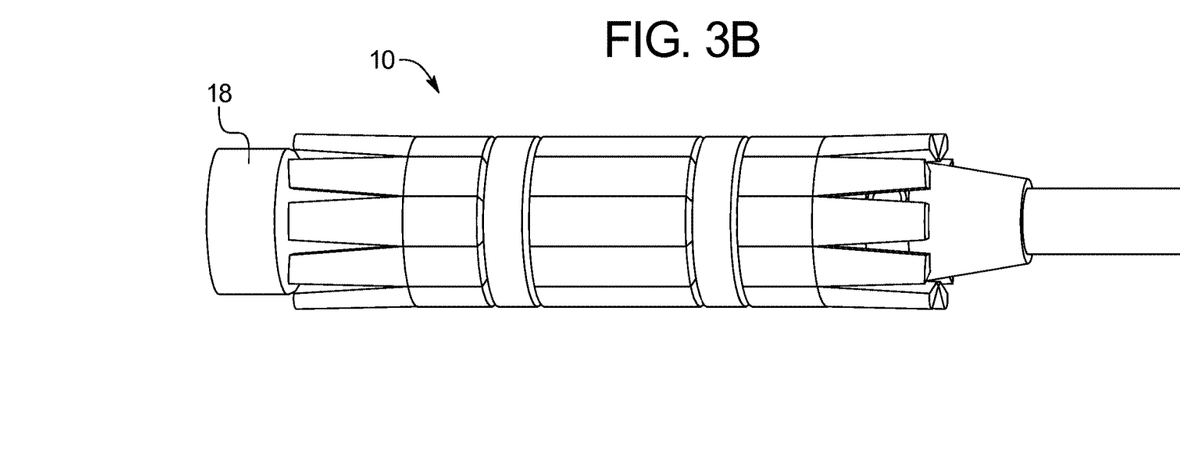
FIG. 3B is a side view of the dilator of FIG. 3A in an expanded configuration.

FIGS. 3A and 3B show a further example of a dilator 10 in collapsed and expanded configurations, respectively, in which both a leading end 18 and a trailing end 20 are configured to enter the passageway. The dilator 10 of FIGS. 3A and 3B is similar to that shown in FIGS. 1A-1F except that the leading end 18 is configured to enter the segmented body 22 and the trailing end 20 is configured to enter the segmented body 22. Further description regarding configurations of the leading end 18 and the trailing end 20 is provided below. For example, configurations of the leading end 18 and the trailing end 20 are described with regard to selecting only one of the leading end 18 or the trailing end 20 or selecting both the leading end 18 and the trailing end 20 to be able to enter the passageway 26 of the segmented body 22.

The leading end 18 and/or the trailing end 20 may be configured to enter the passageway 26 of the segmented body 22. Thus, the leading end 18 and/or the trailing end 20 may apply an outward radial force to the segmented body 22. For example, a proximal portion of the leading end 18 and/or a distal portion of the trailing end 20 may be angled or tapered. For instance, an outer surface of a distal portion of the trailing end 20 may be angled radially outward from the distal end toward a proximal end of the trailing end 20. Thus, the segments 25 may move or slide along the outer surface as the trailing end 20 moves further into the passageway 26. The angle of the outer surface may be selected based on how far the segments 25 are selected to be able to extend radially outward. In addition, the angle of the outer surface may provide varying degrees of radial expansion. Thus, as the trailing end 20 moves further into the passageway 26, the segments 25 may move further radially outward.

Moreover, when the trailing end 20 is configured to expand a proximal portion of the segmented body 22 while the leading end 18 does not expand the distal portion of the segmented body 22, an outer surface of the segmented body 22 may form a frustoconical shape with the distal portion of the segmented body 22 having a circumference or a diameter smaller than a circumference or a diameter of a proximal portion of the segmented body 22. The frustoconical shape may facilitate movement of the dilator 14 into and/or through a body opening or channel while the proximal portion of the segmented body 22 is expanded.

Similarly, an outer surface of a proximal portion of the leading end 18 may be angled radially outward from the proximal portion toward a distal portion of the leading end 18. Thus, the leading end 18 may function similarly as that described with regard to the trailing end 20.

The leading end 18 or the trailing end 20 may be configured to not enter the passageway 26 so that the leading end 18 or the trailing end 20 does not apply an outward radial force to the segmented body 22. For example, the leading end 18 may have a proximal portion or the trailing end 20 may have distal portion that is generally perpendicular to the leading stem 24 (e.g., non-angled or non-tapered) that extends radially outward beyond the passage 26 and/or the segmented body 22. The distal portion or the proximal portion may have other configurations that prevent the trailing end 20 or the leading end 18, respectively, from entering the passageway 26. For example, the leading end 18 or the trailing end 20 may include a ridge 33 such as an annular ridge that extends radially outward beyond the segmented body 22 and extends longitudinally toward the segmented body 22. The ridge 33 may prevent radial outward movement of the either the distal end or the proximal end of the segments 25. Therefore, only the portions of the segments 25 that are not restricted may move radially outward. When one end of the segmented body 22 is restricted from expanding radially outward and when in the expanded configuration, the segmented body 22 may form an outer surface that is angled either inward from the distal end toward the proximal end or inward from the proximal end toward the distal end, as described above.

The portions of the leading end 18 and the trailing end 20 that are furthest from the segmented body 22 may also be angled or tapered. For example, an outer surface of the distal portion of the leading end 18 may be angled radially outward from the distal portion toward the proximal portion of the leading end 18. The angled or tapered distal portion of the leading end 18 may facilitate insertion of the dilator 10 into a body opening or channel. Furthermore, an outer surface of the proximal portion of the trailing end 20 may be angled radially outward from the proximal portion toward the distal portion of the trailing end 20. The angled or tapered proximal portion of the trailing end 20 may provide a smooth transition to facilitate removal of the dilator 10 from a body opening or channel.

The sheath 12 may restrict the outward radial movement of the segmented body 22 so that the segmented body 22 remains engaged with the leading end 18 and the trailing end 20. For instance, the sheath 12 may provide an inward radial force onto the segments 25 of the segmented body 22. For example, as described above, the sheath 12 may be elastic. Alternatively or in addition, the dilator 10 may include one or more elastic members 34 such as elastic bands disposed about the segmented body 22 to restrict outward radial movement of the segments 25. The elastic members 34 may be a polymer such as rubber or any other material described above with regard to the elastic material of the sheath 12. Furthermore, the elastic members 34 may be disposed within a groove 36 such as an annular groove of the segmented body 22 to restrict longitudinal movement of the elastic members 34.

The segmented body 22 illustrated in FIGS. 1A-1F comprises a plurality of segments 25 disposed circumferentially around the passage 26 and the leading stem 24. The segments 25 may be separate components or separate pieces from one another. Thus, the segments 25 may be disengageable from one another. The segments 25 may be elongated members that extend generally longitudinally along an axis of the leading stem 24. For example, each segment 25 may have a length greater than a width and/or a length greater than a thickness. As the segments 25 expand outward radially, the segments 25 may separate from one another. Therefore, a space may form between neighboring segments 25 during expansion. However, as described above, the dilator system 10 may include a sheath 12 that covers the dilator 14 to prevent tissue from entering the spaces between neighboring segments 25.

To facilitate movement of the dilator system 10 through a body opening or channel, an outer surface of the segmented body 22 may be generally smooth. For example, an outer surface of a proximal portion of the segmented body 22 may be angled radially outward from the proximal portion toward the distal portion, and/or an outer surface of a distal portion of the segmented body 22 may be angled radially outward from the distal portion toward the proximal portion.

Figure 8:
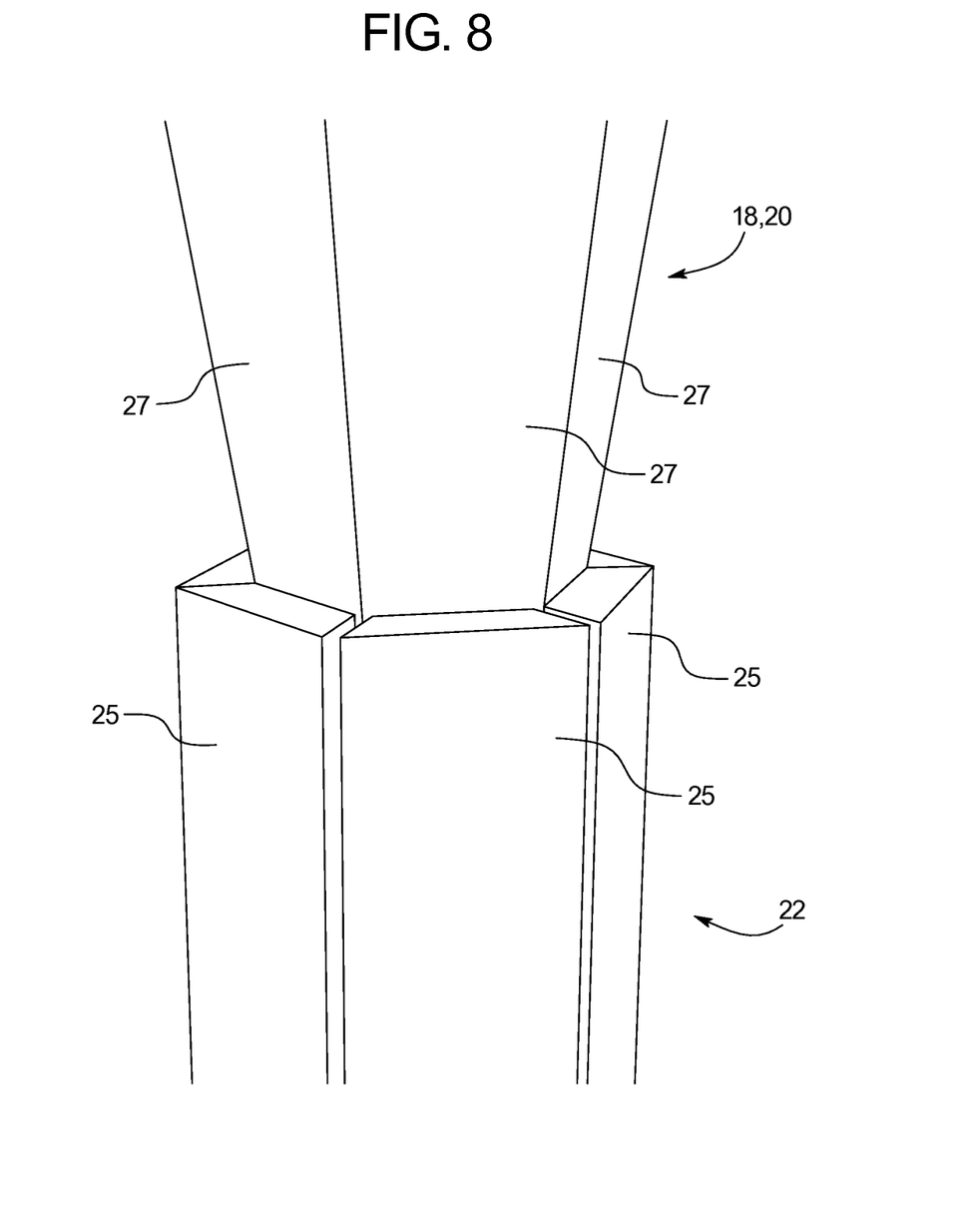
FIG. 8 is a perspective view of a trailing or leading end having ramp sections that engage with the segmented members of the segmented body.

The segmented body 22 may be further configured to restrict rotational movement about the leading stem 24. For example, the segmented body 22 may have at least one of a groove or a protrusion extending longitudinally within the passageway 26. At least one of the leading end 18 or the trailing end 20 may have a groove or a protrusion that engages with the groove or the protrusion of the segmented member 25 to restrict rotational movement of the segmented body 22. For instance, the segmented body 22 may have a groove and the leading end 18 or the trailing end 20 may have a protrusion configured to engage with the groove. Alternatively, the leading end 18 or the trailing end 20 may have a groove and the segmented body 22 may have a protrusion configured to engage with the groove. Thus, the combination of the groove that extends longitudinally along with the protrusion may allow longitudinal movement while restricting or preventing rotational movement of the segmented body 22 relative to the leading end 18 and/or the trailing end 20. FIG. 8 illustrates another example of a leading or trailing end 18, 20 configured to restrict rotational movement of the segmented body 22 about the leading or trailing end 18, 20. The leading or trailing end 18, 20 can have an outer surface with separate ramp sections 27 that correspond to separate segmented members 25. Each ramp section 27 can be substantially flat. The inner surface of each of the segmented members 25 can also be substantially flat.

Figure 4:
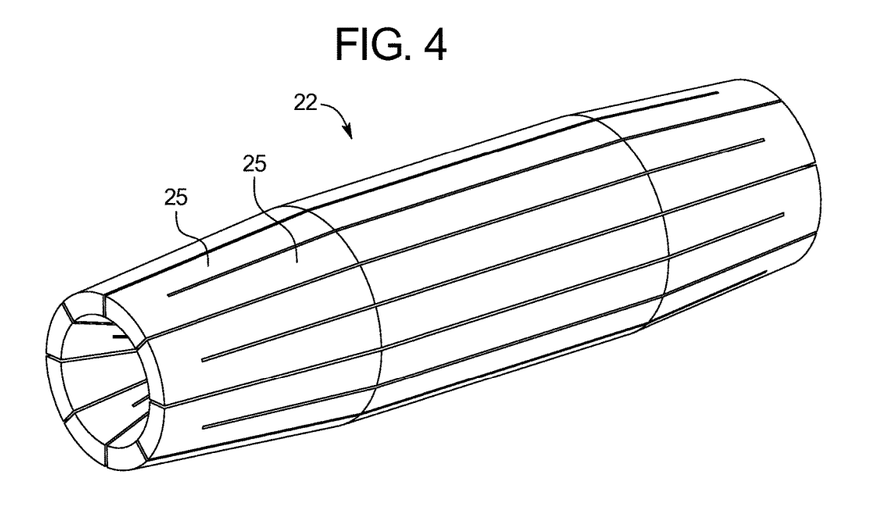
FIG. 4 is a perspective view of a segmented member having a plurality of segments coupled to one another according to an embodiment of the present application.

The segments 25 may remain at least partially engaged with neighboring segments 25. For example, the segments 25 may be an integral single component or piece. In FIG. 4, an example segmented body 22 is shown that is formed of a single piece. The segments 25 may be coupled to neighboring segments 25 at either the distal portion or the proximal portion of the segments 25. For example, the segments 25 may be connected to one another at only one of a distal end or a proximal end so that neighboring segments 25 are separable at an opposite end. As illustrated in FIG. 4, each segment 25 may be sandwiched between two other segments 25. Each segment 25 may be coupled to one neighboring segment 25 at the distal end and coupled to the other neighboring segment 25 at the proximal end. Even though the segments 25 may be coupled to one another, the segments 25 are capable of expanding radially outwardly.

Furthermore, the segments 25 may be formed of an elastic, semi-elastic or rigid material such as nylon or metal. Example metals can include stainless steel, titanium ASTM F63-83 Grade 1, or niobium. Example stainless steels include 304 and 316L stainless steel. Such stainless steels can be corrosion resistant with a low carbon content and additions of molybdenum and niobium. Other materials that may have similar characteristics to stainless steel include tantalum, platinum alloys, niobium alloys and cobalt alloys. If the segments 25 are elastic, the dilator 14 may not include elastic members 34 since the segments 25 may themselves provide a contracting or radially inward force when expanded. For example, the segmented body 22 of FIG. 4 may provide a radial inward force when expanded. If only one of the distal portion or the proximal portion of the segments 25 is configured to be expanded, the segments 25 may be coupled to one another at the portion configured to not expand (e.g., proximal or distal portion). Therefore, the end portion that the segments 25 are coupled at may not expand radially outward while the other end portion of the segments 25 may expand radially outward.

Figure 5:
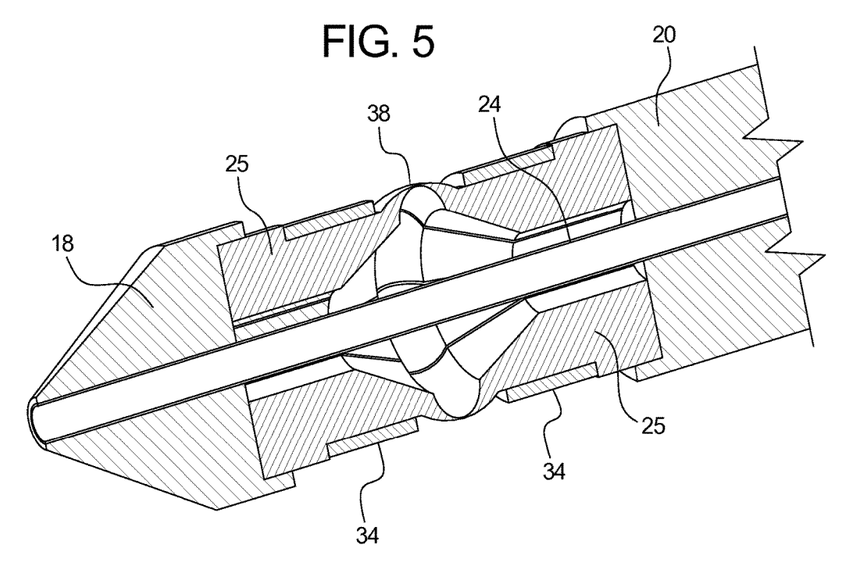
FIG. 5 is a perspective view of a dilator with segments having a living hinge according to an embodiment of the present application.
Figure 6:
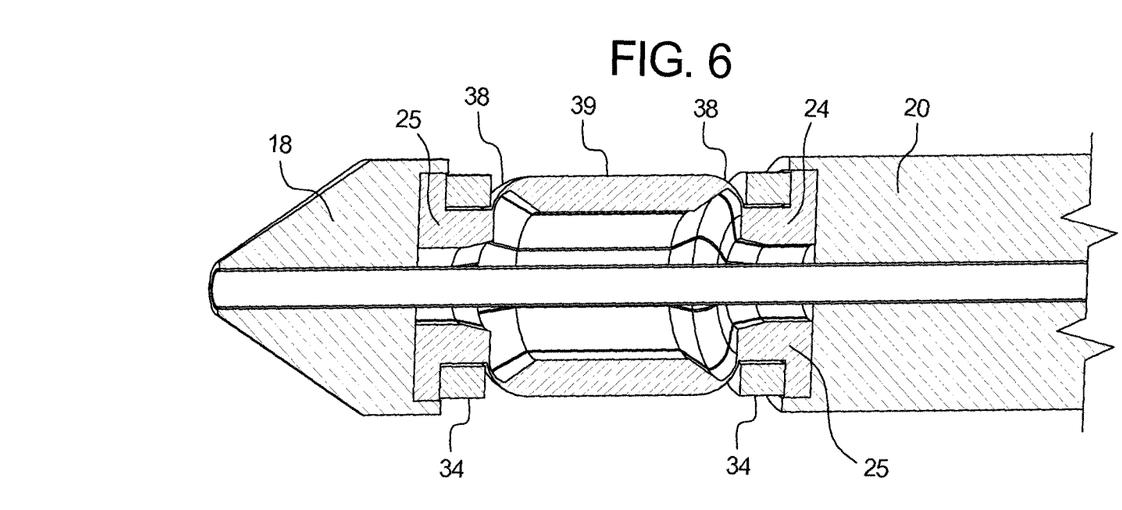
FIG. 6 is a perspective view of a dilator with segments having two living hinges and an expansion region therebetween according to an embodiment of the present application.

In FIG. 5, another example of the dilator 14 is shown with segments 25 that each have a living hinge 38, which may be located at the center of each segment 25. With this arrangement, it may be desirable for the leading end 18 to be designed as shown in FIG. 1E and the trailing end 20 to be designed as shown in FIG. 2A. That is, the leading and trailing ends 18, 20 do not enter the segmented body 22 to expand the segmented body 22 radially outward. Instead, the leading and trailing ends 18, 20 contact the respective ends of the segmented body 22 allowing the leading and trailing ends 18, 20 to exert longitudinal compression on the segmented body 22. As a result, the segments 25 will pivot outward about the living hinge 38. As previously described, elastic members 34 may be provided to compress the segments 25 when longitudinal compression is not being applied to the segmented body 22. In FIG. 6, each of the segments 25 could be provided with two living hinges 38 spaced longitudinally apart to form an expansion region 39 between the living hinges 38. Thus, when longitudinal compression is applied to the segmented body 22, each of the living hinges 38 will pivot outward. This causes the expansion region 39 to move radially outward while remaining generally parallel to the axis of the dilator 14. Although the living hinge 38 arrangement may be particularly desirable with separate segments 25 as shown in FIGS. 5-6, it is understood that the living hinge 38 expansion described here could also be used with the single component segmented body 22 of FIG. 4. It is also understood that in place of elastic members 34 to compress the segmented body 22 the respective ends of the segmented body 22 could be attached to the leading and trailing ends 18, 20. Thus, the segmented body 22 could be compressed by pulling the leading and trailing ends 18, 20 apart and stretching the segmented body 22.

Figure 7:
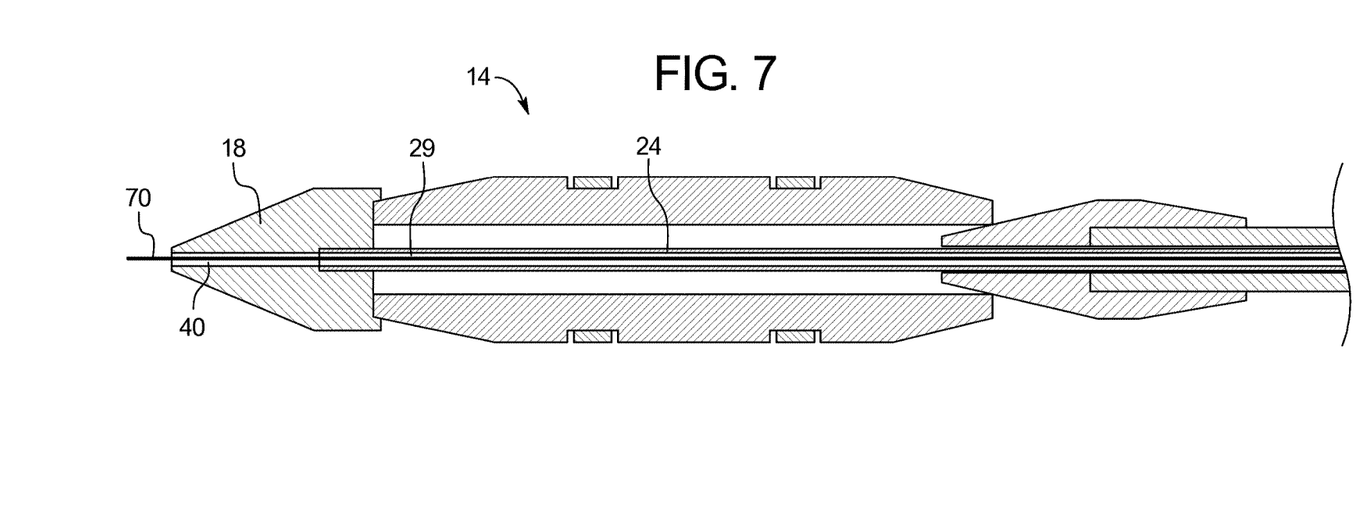
FIG. 7 is a side view of the dilator of FIG. 1C showing a guide wire extending through the dilator.

As illustrated in FIGS. 1E and 1F, the leading end 18 may include an opening 40 extending from a distal end to the proximal end. The leading stem 24 may include a channel 29 extending from a distal end to a proximal end. For example, the leading stem 24 may be an elongated tube. The opening 40 of the leading end 18 may be continuous with or in fluid communication with the channel 29 of the leading stem 24. Therefore, a guide wire 70 may be positioned at least partially within the channel 29 of the leading stem 24 and the opening 40 of the leading end 18, as illustrated in FIG. 7. If the dilator system 10 also includes a sheath 12, the sheath 12 may include an opening in a distal end so that the guide wire 70 may extend out of the distal end of the dilator system 10. As such, the guide wire 70 may be used to reach a target site within a body opening or channel, and the dilator system 10 may slide over the guide wire 70 so that the dilator system 10 may more easily reach the target site. Furthermore, the opening 40 of the leading end 18 and the channel 29 of the leading stem 24 may provide a passage through the dilator system 10. Therefore, the passage through the dilator system 10 may provide an airway for a patient during a tracheostomy procedure, as described below, or may provide a passage to deliver a fluid to within the body opening or channel.

The dilator system 10 may be used in various medical procedures to open or dilate a body opening or channel. For instance, the dilators 10 described herein may replace the function of hydraulic balloons in the medical field. The dilator systems 10 described herein may be safer than a dilator that includes a hydraulic balloon since a fluid is not needed to expand the dilator 14. In particular, hydraulic balloons may burst or fail possibly causing damage to a patient. In addition, the force that a hydraulic balloon may be able to apply to a body opening or channel may be limited. The dilator systems 10 described herein may be able to provide more force on a body opening or channel than a hydraulic balloon without failure. Furthermore, the dilator system 10 may provide a large range of adjustable sizes.

In one example, the dilator system 10 may be a tracheal dilator. A tracheal dilator may be used to expand a stoma such as in a tracheostomy procedure. Different sized tracheal dilators are often used in a tracheostomy procedure. For instance, a first size may be selected, but the user may decide that a different size may be more appropriate. The user may than discard the first tracheal dilator and use a second tracheal dilator having a different size. The size of the dilator system 10 described herein may be adjustable; therefore, a single dilator system 10 may be used even if different sizes are used or needed during the procedure.

In another example, the dilator system 10 may be a vascular dilator. A vascular dilator may be inserted into a vessel and navigated to a target site. The vascular dilator may then be expanded to dilate the target site. For instance, the target site may have plaque buildup that may be pushed or compressed toward the walls of the vessel with the dilator 10 to flatten the plaque and increase the opening size of the vessel.

Although certain examples of types of dilators and medical procedures are described above, the dilator systems 10 described herein can be other types of dilators and used in other medical procedures. For example, the dilator system 10 described herein can be used in procedures that other types of mechanical dilators and balloon dilators are used in. Other non-limiting examples include stricture dilation, esophageal dilation, angioplasty, fibrosis dilation, lymphatic dilation, etc.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A dilator comprising:
    a leading portion comprising a leading end coupled to a leading stem;
    a trailing portion comprising a trailing end coupled to a trailing shaft, the trailing end having an opening, and the trailing shaft having a channel; and
    a segmented body disposed between the leading end and the trailing end, the segmented body having a passageway extending between a proximal end and a distal end, and the segmented body comprising a plurality of segments disposed circumferentially around the leading stem,
    wherein the leading stem extends through the passageway of the segmented body, the opening of the trailing end and the channel of the trailing shaft, and the leading stem and the trailing shaft are configured to move longitudinally and independently relative to one another so that at least one of the leading end or the trailing end enters the passageway of the segmented body to radially outwardly expand the segmented body.

2. The dilator of claim 1, wherein an outer surface of a proximal portion of the leading end is angled radially outward from the proximal portion toward a distal portion of the leading end.

3. The dilator of claim 2, wherein an outer surface of the distal portion of the leading end is angled radially outward from the distal portion toward the proximal portion of the leading end.

4. The dilator of claim 1, wherein an outer surface of a distal portion of the trailing end is angled radially outward from the distal portion toward a proximal portion of the trailing end.

5. The dilator of claim 4, wherein an outer surface of the proximal portion of the trailing end is angled radially outward from the proximal portion toward the distal portion of the trailing end.

6. The dilator of claim 1, wherein both the leading end and the trailing end are configured to enter the passageway of the segmented body.

7. The dilator of claim 1, wherein the trailing end is configured to expand a proximal portion of the segmented body while the leading end does not expand a distal portion of the segmented body such that an outer surface of the segmented body forms a frustoconical shape with the distal portion of the segmented body having a diameter smaller than a diameter of a proximal portion of the segmented body.

8. The dilator of claim 1, wherein the plurality of segments are separate pieces.

9. The dilator of claim 1, wherein the plurality of segments are connected to one another at only one of a distal portion or a proximal portion so that neighboring segments are separable at an opposite end.

10. The dilator of claim 1, wherein the plurality of segments are connected at a distal portion to the leading end.

11. The dilator of claim 1, wherein the plurality of segments and the leading end are a single piece structure.

12. The dilator of claim 1, wherein the leading stem comprises a channel extending between a distal end and a proximal end.

13. The dilator of claim 12, wherein the leading end comprises a channel extending between a distal end and a proximal end of the distal member, and the channel of the leading end is in fluid communication with the channel of the leading stem.

14. The dilator of claim 1, wherein the segmented body comprises at least one of a groove or a protrusion extending longitudinally within the passageway, and at least one of the leading end or the trailing end comprises a groove or a protrusion that engages with the groove or the protrusion of the segmented body to restrict rotational movement of the segmented body.

15. A dilator system comprising:
    a elastic sheath;
    a dilator at least partially disposed within the elastic sheath, the dilator comprising:
    a leading portion comprising a leading end coupled to a leading stem;
    a trailing portion comprising a trailing end coupled to a trailing shaft, the trailing end having an opening, and the trailing shaft having a channel; and
    a segmented body disposed between the leading end and the trailing end, the segmented body having a passageway extending between a proximal end and a distal end, and the segmented body comprising a plurality of segments disposed circumferentially around the leading stem,
    wherein the leading stem extends through the passageway of the segmented body, the opening of the trailing end and the channel of the trailing shaft, and the leading stem and the trailing shaft are configured to move longitudinally and independently relative to one another so that at least one of the leading end or the trailing end enters the passageway of the segmented body to radially outwardly expand the segmented body.

16. The dilator system of claim 15, wherein the elastic sheath surrounds an entire length of the segmented body and is bonded to the leading end and the trailing shaft.

17. The dilator system of claim 15, wherein the elastic sheath restricts fluid flow into the dilator.

18. The dilator system of claim 15, further comprising a guide wire extending through the dilator.

19. The dilator system of claim 15, wherein the dilator system is a vascular dilator.

20. The dilator system of claim 15, wherein the dilator system is a tracheal dilator.

* * * * *